United States Patent
Huang et al.

(10) Patent No.: US 8,598,351 B2
(45) Date of Patent: Dec. 3, 2013

(54) PHOSPHO-AMINO PINCER-TYPE LIGANDS AND CATALYTIC METAL COMPLEXES THEREOF

(75) Inventors: Kuo-Wei Huang, Thuwal (SA); Tao Chen, Wuhan (CN); Lipeng He, Beijing (CN); Dirong Gong, Shangyu (CN); Weiguo Jia, Wuhu (CN); Liangfeng Yao, Suzhou (CN)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 13/528,481

(22) Filed: Jun. 20, 2012

(65) Prior Publication Data
US 2012/0323007 A1 Dec. 20, 2012

Related U.S. Application Data

(60) Provisional application No. 61/499,028, filed on Jun. 20, 2011.

(51) Int. Cl.
| | |
|---|---|
| *C07F 13/00* | (2006.01) |
| *C07C 67/00* | (2006.01) |
| *C07C 249/00* | (2006.01) |
| *C07F 9/58* | (2006.01) |

(52) U.S. Cl.
USPC .............. 546/2; 546/22; 560/1; 564/248

(58) Field of Classification Search
None
See application file for complete search history.

(56) References Cited

U.S. PATENT DOCUMENTS

| 8,178,723 B2 | 5/2012 | Milstein et al. ............... 564/123 |
| 2009/0112005 A1 | 4/2009 | Milstein et al. ............... 549/493 |
| 2010/0236984 A1 | 9/2010 | Brookhart et al. ............ 208/121 |

OTHER PUBLICATIONS

Poverenov et al., Pincer "Hemilabile" Effect. PCN Platinum (II) Complexes with Different Amine "Arm Length", 24 Organometallics 1082-1090 (2005).*

Jung et al., Synthesis of Novel Pd-NCN Pincer Complexes Having Additional Nitrogen Coordination Sites and Their Application as Catalysts for the Heck Reaction, 22 Organometallics 4715-4720 (2003).*

* cited by examiner

*Primary Examiner* — Janet L Andres
*Assistant Examiner* — Timothy R Rozof
(74) *Attorney, Agent, or Firm* — Fulbright & Jaworski LLP

(57) ABSTRACT

The present invention provides phospho-amino pincer-type ligands, metal complexes thereof, and catalytic methods comprising such metal complexes.

29 Claims, 7 Drawing Sheets

PHOSPHO-AMINO PINCER-TYPE LIGANDS AND CATALYTIC METAL COMPLEXES THEREOF

This application claims the benefit of priority to U.S. Provisional Patent Application No. 61/499,028, filed Jun. 20, 2011, the contents of which are incorporated herein by reference in their entirety.

BACKGROUND OF THE INVENTION

I. Field of the Invention

The present invention relates generally to the field of chemistry and catalysis. More particularly, it relates to phospho-amino pincer-type ligands, metal complexes thereof, and catalytic methods comprising such metal complexes.

II. Description of Related Art

Pincer-type transition metal complexes have been studied in the last decade (Jensen, 2007; van der Boom and Milstein, 2003). The pincer ligand systems provide a number of desirable properties. They can coordinate to metal to form metallocycles with excellent thermal stability and the reactivity of these complexes have been found to vary with the structure/substituent of the pincer ligands. Moreover, pincer-type transition metal complexes have found useful applications in many fields, especially in catalysis, including for the catalytic hydrogenation of carbon dioxide (Tanaka et al., 2009), catalytic dehydrogenation of alkane (Gupta et al., 1996; Gupta et al., 1997; Xu et al., 1997; Liu et al., 1999; Haenel et al., 2001; Ray et al., 2005; Goldman et al., 2006), catalytic hydrogenation of ketone (Langer et al., 2011), or direct synthesis of amides from alcohols and amines (Gunanathan et al., 2007; Milstein et al., 2008; Gnanaprakasam et al., 2010; Gunanathan et al., 2010; Milstein, 2010; Gnanaprakasam and Milstein, 2011). In view of these advances, it would be desirable to develop new pincer-type ligands having different properties or profiles from those already known. If successful, such attempts would provide a greater palette of such ligands, which would expand the options available to a chemist, for example, to allow the best ligand to be selected for given application and/or to extend the use of these ligands to new applications. Similar considerations apply to metal catalysts comprising such ligands, as well as methods of using such metal catalysis. Therefore new pincer-type ligands, especially a novel class of these ligands, and transition metal complexes thereof would be a great advantage.

SUMMARY OF THE INVENTION

In one aspect, the present disclosure provides phospho-amino ligands, including compounds according to Formula I:

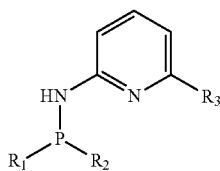

(I)

wherein:
R$_1$ and R$_2$ are each independently alkyl$_{(C\leq 12)}$, aryl$_{(C\leq 12)}$, aralkyl$_{(C\leq 12)}$, or a substituted version of any of these groups; and R$_3$ is a group comprising a nitrogen atom that is separated by one atom from the carbon atom to which R$_3$ is connected.

In some embodiments, the compound of claim 1, wherein R$_1$ and R$_2$ are each alkyl$_{(C\leq 8)}$, for example, each tert-butyl.

In some embodiments, R$_3$ is selected from the group consisting of formulas:

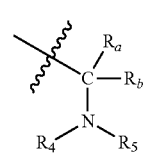

(a)

wherein:
R$_a$ and R$_b$ are each independently hydrogen or fluoro; and
R$_4$ and R$_5$ are each independently alkyl$_{(C\leq 8)}$, aryl$_{(C\leq 8)}$, aralkyl$_{(C\leq 8)}$, or a substituted version of any of these groups;

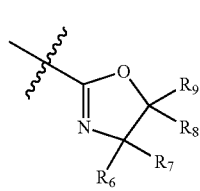

(b)

wherein:
R$_6$, R$_7$, R$_8$ and R$_9$ are each independently:
hydrogen; or
alkyl$_{(C\leq 8)}$, aryl$_{(C\leq 8)}$, aralkyl$_{(C\leq 8)}$, or a substituted version of any of these groups;

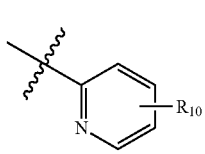

(c)

wherein:
R$_{10}$ is:
hydrogen, hydroxy, amino, halo, nitro; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups;

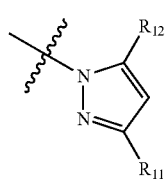

(d)

wherein:
R$_{11}$ and R$_{12}$ are each independently:
hydrogen; or alkyl$_{(C\leq 8)}$, aryl$_{(C\leq 8)}$, aralkyl$_{(C\leq 8)}$, or a substituted version of any of these groups; and

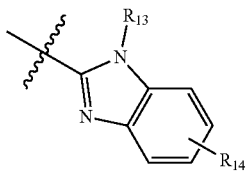

(e)

wherein:

$R_{13}$ is hydrogen, alkyl$_{(C\leq 8)}$ or substituted alkyl$_{(C\leq 8)}$; and $R_{14}$ is:

hydrogen, hydroxy, amino, halo, nitro; or alkyl$_{(C\leq 8)}$, alkoxy$_{(C\leq 8)}$, alkylamino$_{(C\leq 8)}$, dialkylamino$_{(C\leq 8)}$, or a substituted version of any of these groups;

and a salt or tautomer thereof.

In some embodiments, $R_3$ is formula (a). In some embodiments, $R_a$ and $R_b$ are hydrogen. In some embodiments, $R_4$ and $R_5$ are each alkyl$_{(C\leq 8)}$. In some embodiments, the compound is further defined as:

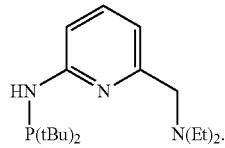

In some embodiments, $R_3$ is formula (b). In some embodiments, $R_6$ and $R_7$ are each alkyl$_{(C\leq 8)}$, for example, each methyl. In some embodiments, $R_8$ and $R_9$ are each hydrogen. In some embodiments, the compound is further defined as:

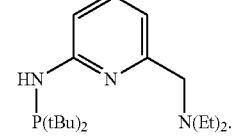

In some embodiments, $R_3$ is formula (c). For example, in some embodiments, the compound is further defined as:

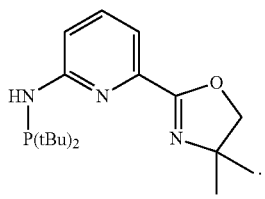

In some embodiments, $R_3$ is formula (d). For example, in some embodiments, the compound is further defined as:

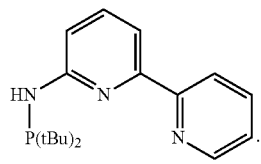

In some embodiments, $R_{11}$ and $R_{12}$ are each alkyl$_{(C\leq 8)}$. For example, in some embodiments, the compound is further defined as:

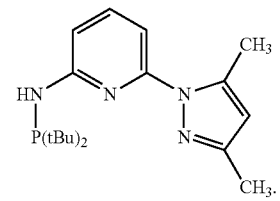

In some embodiments, $R_{11}$ and $R_{12}$ are each aryl$_{(C\leq 8)}$. For example, in some embodiments, the compound is further defined as:

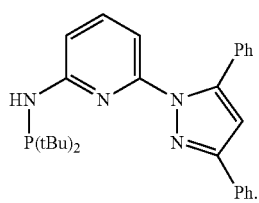

In some embodiments, $R_3$ is formula (e). In some embodiments, $R_{13}$ is alkyl$_{(C\leq 8)}$. For example, in some embodiments, the compound is further defined as:

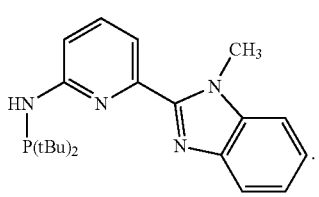

In another aspect of the present disclosure, there are provided complexes comprising a ligand and a metal or metal ion, wherein the ligand is any of the above compounds or a deprotonated form thereof, and the ligand is chemically bound to the metal or metal ion in a 1:1 ratio.

In some embodiments, the metal is a group 8 metal or metal ion, for example, ruthenium. In some embodiments, the complex further comprises a second ligand, wherein the second ligand is chloride. In some embodiments, the complex further comprises a third ligand, wherein the third ligand is carbon monoxide. For example, in some embodiments, the complex is further defined as:

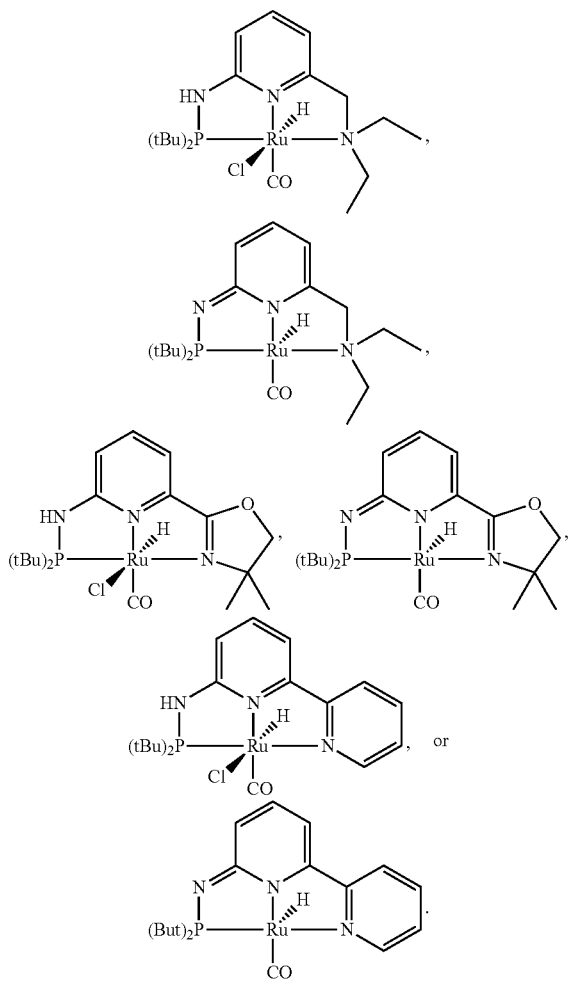

In some embodiments, the metal is a group 9 metal or metal ion, for example, cobalt. In other embodiments, the metal is a group 10 metal or metal ion, for example, nickel or palladium.

In another aspect of the present disclosure, there are provided methods for the preparation of an ester of Formula III comprising reacting two or more alcohols of Formula II:

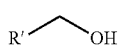 (II)

in the presence of a catalyst to make an ester of Formula III:

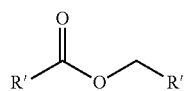 (III)

wherein:
R' is alkyl$_{(C≤8)}$, substituted alkyl$_{(C≤8)}$, aryl$_{(C≤8)}$, substituted aryl$_{(C≤8)}$, aralkyl$_{(C≤8)}$ or substituted aralkyl$_{(C≤8)}$; and
the catalyst is any of the above complexes.

In another aspect of the present disclosure, there are provided methods for the preparation of an imine of Formula V comprising reacting two or more alcohols of Formula II:

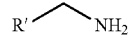 (IV)

in the presence of a catalyst to make an imine of Formula V:

 (V)

wherein:
R' is alkyl$_{(C≤8)}$, substituted alkyl$_{(C≤8)}$, aryl$_{(C≤8)}$, substituted aryl$_{(C≤8)}$, aralkyl$_{(C≤8)}$ or substituted aralkyl$_{(C≤8)}$; and
the catalyst is any of the above complexes.

In another aspect of the present disclosure, there are provided methods for the preparation of an alcohol of Formula VII comprising reacting a ketone of Formula VI:

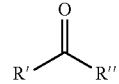 (VI)

in the presence of a catalyst and a secondary alcohol to make an alcohol of Formula VII:

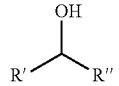 (VII)

wherein:
R' and R" are each independently alkyl$_{(C≤8)}$, substituted alkyl$_{(C≤8)}$, aryl$_{(C≤8)}$, substituted aryl$_{(C≤8)}$, aralkyl$_{(C≤8)}$ or substituted aralkyl$_{(C≤8)}$; and
the catalyst is any of the above complexes.

In another aspect of the present disclosure, there are provided methods for the preparation of a coupling product of Formula X comprising reacting a first compound of Formula VIII:

 (VIII)

with a second compound of Formula IX:

 (IX)

in the presence of a catalyst to make a coupling product of Formula X:

 (X)

wherein:
R' and R" are each independently aryl$_{(C≤16)}$ or substituted aryl$_{(C≤16)}$; and
the catalyst is any of the above complexes.

In another aspect of the present disclosure, there are provided methods for the preparing a polyolefin, comprising polymerizing an alkene$_{(C≤16)}$ or a substituted alkene$_{(C≤16)}$ in the presence of a catalyst to make a polyolefin, wherein the catalyst is any one of the above complexes. In some embodiments, the alkene is 1,3-butadiene. In some embodiments, the polyolefin microstructure is at least 98% cis-1,4.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1:
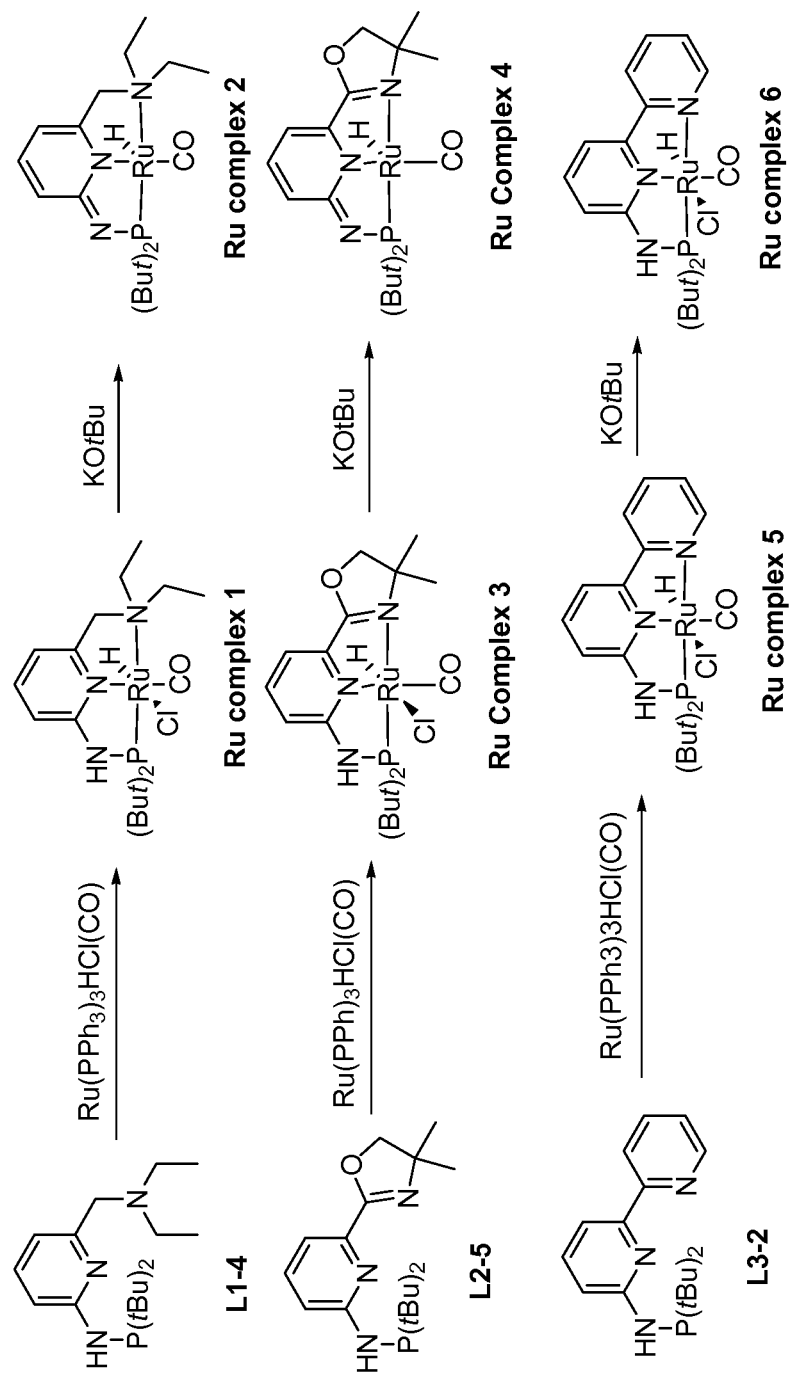
FIG. 1 depicts synthetic schemes for the preparation and deprotonation of Ru complexes comprising an phospho-amino pincer-type ligand.

In certain aspects of the present invention, there are provided a new class of pincer-type ligands, including those having a disubstituted-phosphinoamino (NH—PR$_2$) arm. Metal complexes of such ligands are also provided, including complexes that may be used as catalysts for a variety of transformations, including the dehydrogenation of alcohols, the synthesis of imines from amines, the transfer hydrogenation of ketones and the polymerization of alkenes. Upon complexation to a transition metal and treatment of a base, in some embodiments, the resulting complex can undergo dearomatization after the elimination of H—X.

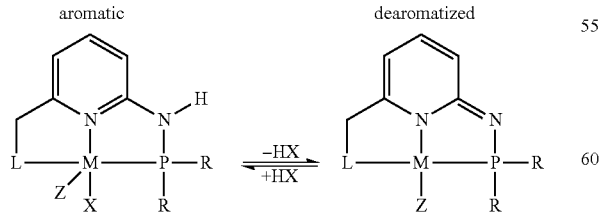

Compared to many if not all previously known CH$_2$—PR$_2$ models, this new system possesses a more acidic proton (N—H) (Bordwell, 1988) as well as a more polar bond (Joule and Mills, 2010) in some embodiments. These properties allow the complexes provided herein to exhibit excellent reactivities towards a variety of substrates.

Selected general structures L1, L2 (X=O, NR), L3, L4, and L5 and examples of reactions catalyzed by the corresponding transition metal complexes are depicted below. Further details regarding different embodiments are provided throughout this disclosure.

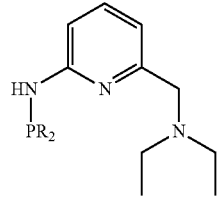

L1

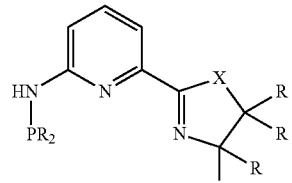

L2

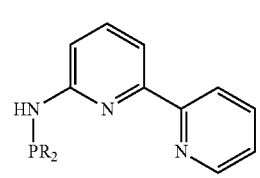

L3

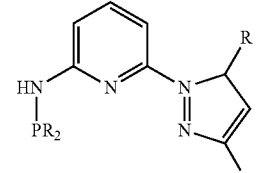

L4

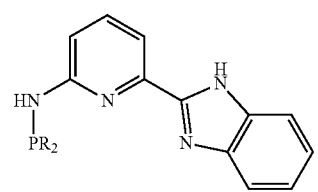

L5

I. Phospho-Amino Pincer-Type Ligands

In one aspect, the invention provides compounds of Formula I:

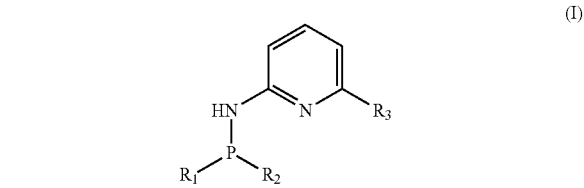

(I)

wherein, R$_1$ and R$_2$ are each independently alkyl$_{(C≤12)}$, aryl$_{(C≤12)}$, aralkyl$_{(C≤12)}$, or a substituted version of any of these groups; and R$_3$ is a group comprising a nitrogen atom that is separated by one atom from the carbon atom to which R$_3$ is connected.

Examples of such ligands and methods of preparing them, and optionally deprotonating them, are provided throughout this disclosure. For example, see FIGS. 3-7 and Example 5.

These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein. The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein.

II. Phospho-Amino, Pincer-Type Ligand Complexes and Methods of Use

The present disclosure also provides metal complexes of this novel class of ligands. Such complexes may be used to facilitate a variety of organic transformations, including catalytic hydrogenation of carbon dioxide (Tanaka et al., 2009), catalytic dehydrogenation of alkane (Gupta et al., 1996; Gupta et al., 1997; Xu et al., 1997; Liu et al., 1999; Haenel et al., 2001; Ray et al., 2005; Goldman et al., 2006), catalytic hydrogenation of ketone (Langer et al., 2011), or direct synthesis of amides from alcohols and amines (Gunanathan et al., 2007; Milstein et al., 2008; Gnanaprakasam et al., 2010; Gunanathan et al., 2010; Milstein, 2010; Gnanaprakasam and Milstein, 2011). These references are incorporated herein in their entireties.

Figure 2:
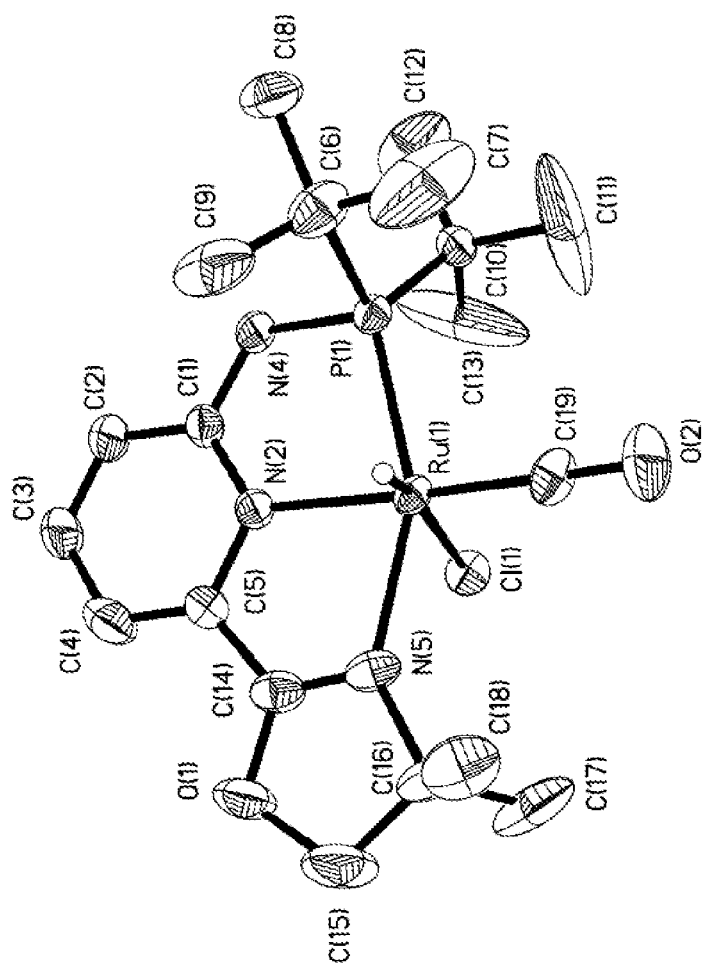
FIG. 2 an Ortep structure of ruthenium complex 3 with thermal ellipsoids drawn at the 30% level. All hydrogen atoms are omitted for clarity except the H—Ru bond.
Figure 3:
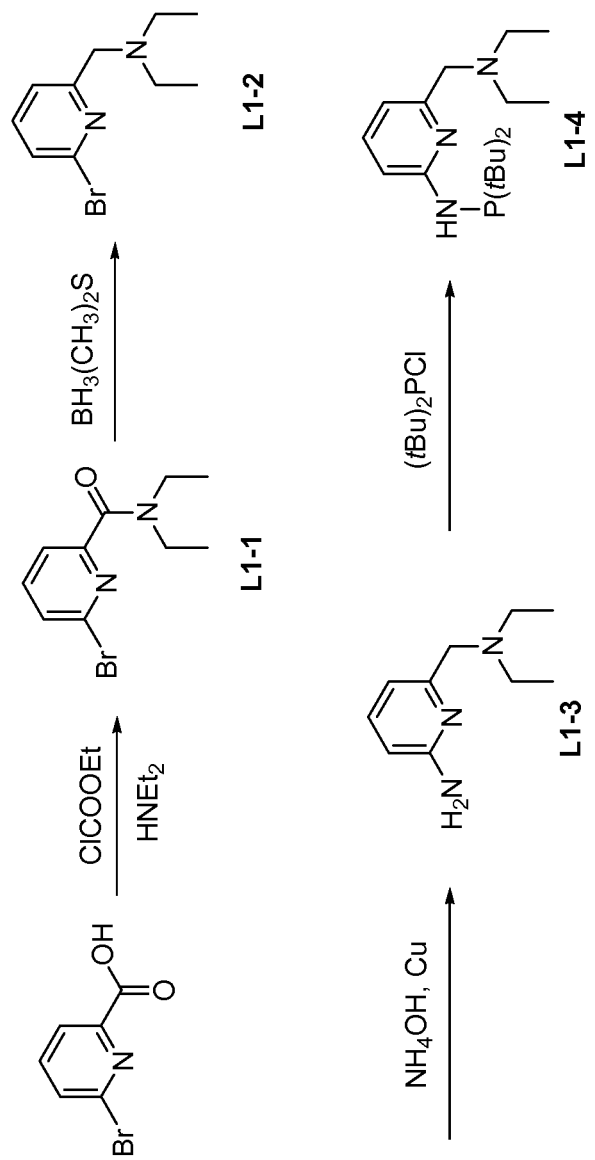
FIG. 3 depicts a synthetic scheme for the preparation of the phospho-amino ligand L1-4.
Figure 4:
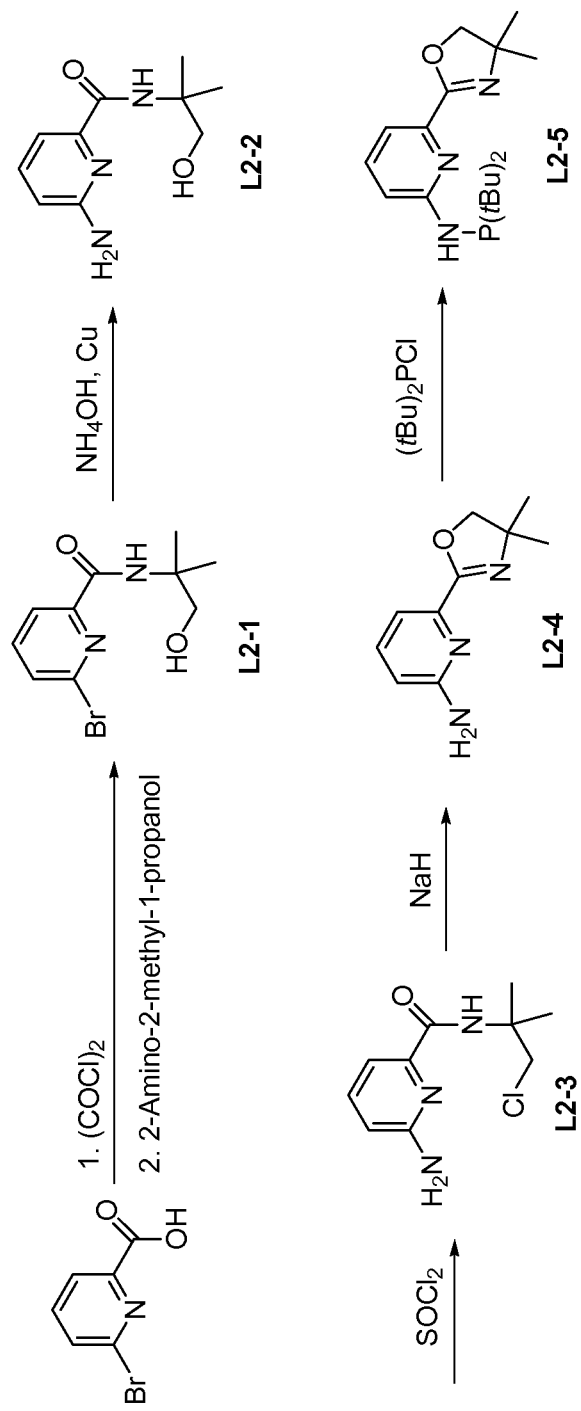
FIG. 4 depicts a synthetic scheme for the preparation of the phospho-amino ligand L2-5.
Figure 5:
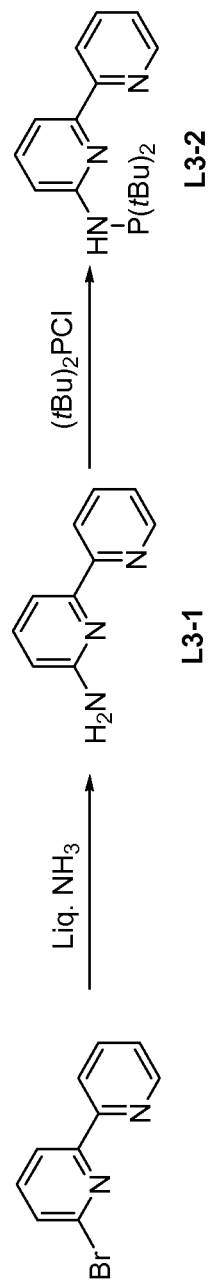
FIG. 5 depicts a synthetic scheme for the preparation of the phospho-amino ligand L3-2.
Figure 6:
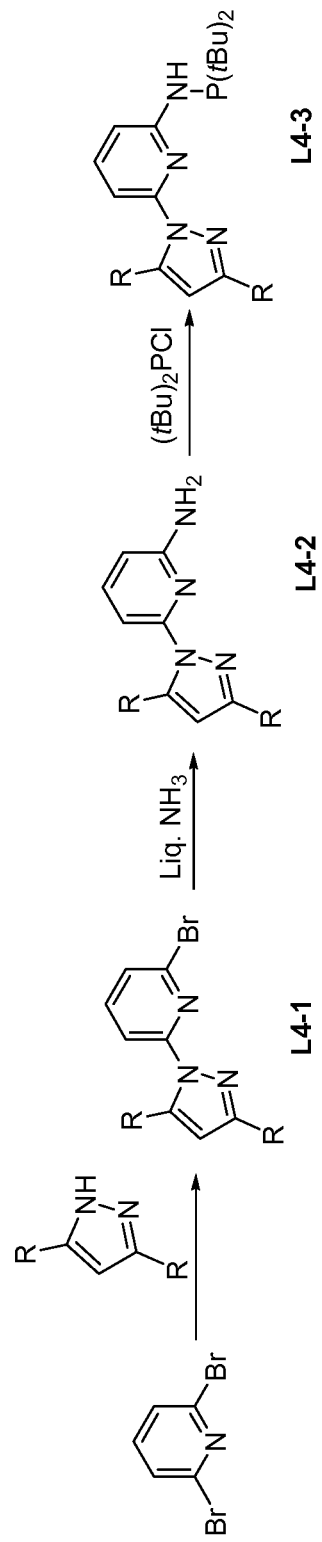
FIG. 6 depicts a synthetic scheme for the preparation of the phospho-amino ligand L4-3.
Figure 7:
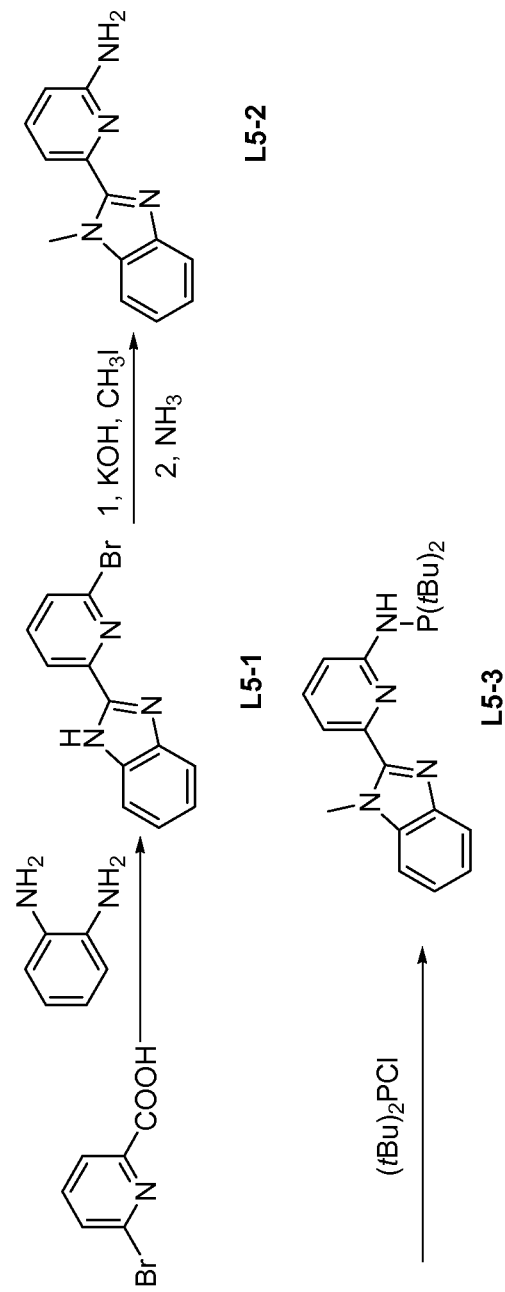
FIG. 7 depicts a synthetic scheme for the preparation of the phospho-amino ligand L5-3.

For example, ruthenium complexes of ligands can be made, and optionally deprotonated, as shown in FIG. 1. Ruthenium complexes of ligands L1, L2 (FIG. 2), and L3 can catalyze, for example, the dehydrogenative homocoupling of alcohols to esters (Table 1), the homocoupling of amines to imines (Table 2), and the transfer hydrogenation of ketones and imines to secondary alcohols and amines (Table 3).

Ni and Pd complexes of these phospho-amino ligands may also be made. See for example, the following scheme.

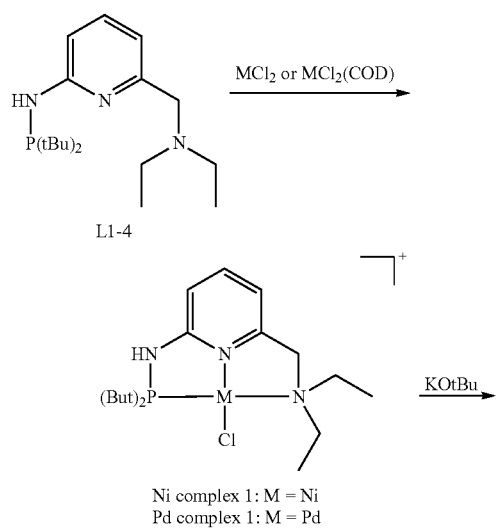

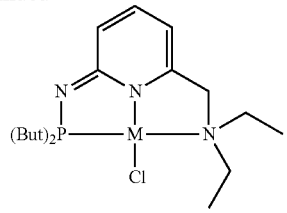

Ni complex 2: M = Ni
Pd complex 2: M = Pd

Such complexes are applicable to a wide variety of organic transformation, including, for example, catalytic cross-coupling reactions, such as the reaction shown in Example 2 below.

In other embodiments, Co complexes may be made using these ligands.

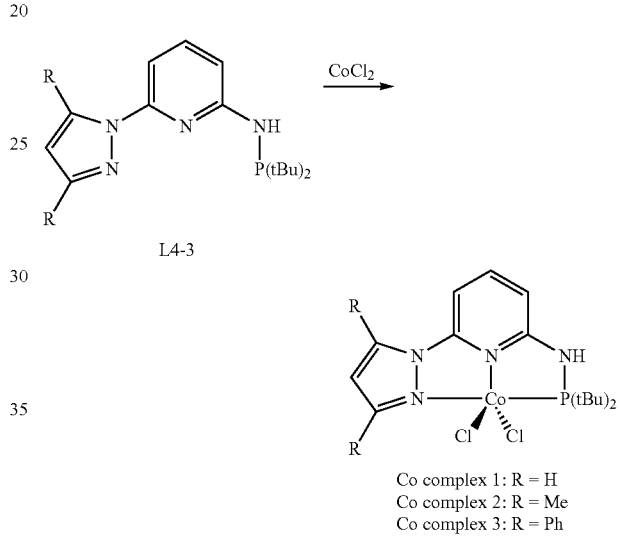

Such complexes may be used to polymerize alkenes. For example, results from a Co complex catalyzed polymerization of butadiene to afford cis-1,4-polybutdiene materials are presented in Example 3 below.

The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein.

III. Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means =S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "sulfinyl" means —S(O)— (see below for definitions of groups containing the term sulfinyl, e.g., alkylsulfinyl).

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the structure

includes the structures

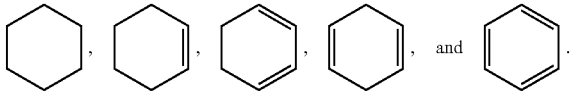

As will be understood by a person of skill in the art, no one such ring atom forms part of more than one double bond. The symbol "〜", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀" means a single bond where the group attached to the thick end of the wedge is "out of the page." The symbol "◁◁◁◁◁" means a single bond where the group attached to the thick end of the wedge is "into the page". The symbol "◁◁◁◁◁" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

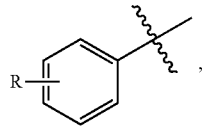

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

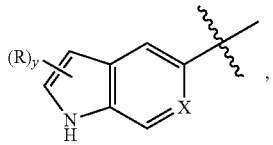

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, CH$_2$CH$_2$CH$_2$—, and

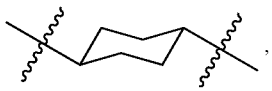 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or not fused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$—CH$_2$CH$_3$ (ethylphenyl), naphthyl, and the monovalent group derived from biphenyl. The term "arenediyl" when used without the "substituted" modifier refers to a divalent aromatic group, with two carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

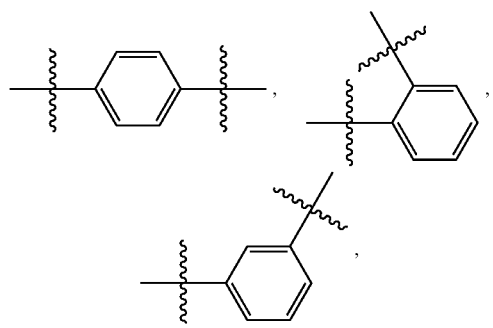

-continued

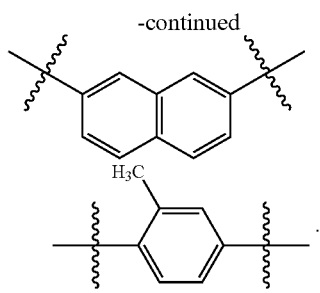

and

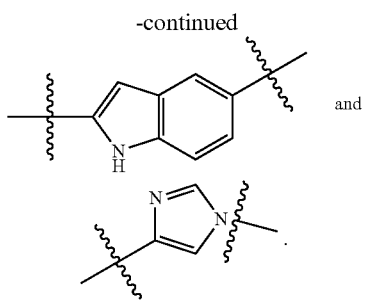

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

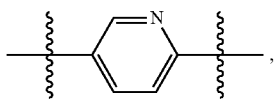

,

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$—CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups —NHC(O)OCH$_3$ and —NHC(O)NHCH$_3$ are non-limiting examples of substituted amido groups.

The above definitions supersede any conflicting definition in any of the reference that is incorporated by reference herein. The fact that certain terms are defined, however, should not be considered as indicative that any term that is undefined is indefinite.

Rather, all terms used are believed to describe the invention in terms such that one of ordinary skill can appreciate the scope and practice the present invention.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Ruthenium Complexes

Ruthenium complexes of ligands L1, L2 (FIG. 2), and L3 can catalyze dehydrogenative homocoupling of alcohols to esters (Table 1), homocoupling of amines to imines (Table 2), and transfer hydrogenation of ketones and imines to secondary alcohols and amines (Table 3). The catalyst loading can be as low as 0.1 mol % and the products were obtained in good to excellent yields.

For catalytic dehydrogenative esterification of primary alcohols, a mixture of Ruthenium complex (0.01 mmol) and alcohol (10 mmol) was heated under an argon flow at the temperature shown in Table 1.

TABLE 1

Dehydrogenation of Primary Alcohols to Esters and H$_2$ Catalyzed by Ru Complex.[a]

$$2\ R\text{—OH} \xrightarrow{\text{Ru complex}} R\text{—C(O)—O—R} + 2H_2$$

| Entry | Substrate | Cat. loading | T (° C.) | Time | Yield[b] |
|---|---|---|---|---|---|
| 1 | 1-butanol | 0.3 mol % | 118 | 12 h | >99% |
| 2 | 1-pentanol | 0.3 mol % | 138 | 12 h | >99% |
| 4 | 1-hexanol | 0.1 mol % | 157 | 24 h | >99% |
| 5 | benzyl alcohol | 0.5 mol % | 160 | 12 h | 94% |
| 6 | 1,5-pentadiol | 1.0 mol % | 160 | 24 h | 80%[c] |

[a]Reaction condition: 0.1-1.0 mol % catalyst in alcohols were heated under argon flow;
[b]Determined by GC-MS and crude $^1$H NMR.
[c]Lactone was formed as the product.

For the catalytic synthesis of an imine from an amine, a mixture of amine (1 mmol) and the ruthenium complex (0.01 mmol) in toluene (2 mL) was heated in to 106° C. in a schlenk flask equipped with a cooling finger under argon atmosphere. Results are shown in Table 2.

TABLE 2

Synthesis of Imine from Amine[a]:

$$2\ R\text{—NH2} \xrightarrow[\text{Toluene, reflux}]{\text{Catalyst (1.0 mol \%)}} R\text{—N=}\text{—R} + H_2 + NH_3$$

| Entry | Amine | T (° C.) | Time (h) | Imine | Yield[b] |
|---|---|---|---|---|---|
| 1 | Ph—CH$_2$—NH$_2$ | 160 | 16 | Ph—CH=N—CH$_2$—Ph | 92% |
| 2 | C$_5$H$_{11}$—NH$_2$ | 120 | 16 | C$_4$H$_9$—CH=N—C$_5$H$_{11}$ | 90% |
| 3 | C$_4$H$_9$—NH$_2$ | 77 | 16 | C$_3$H$_7$—CH=N—C$_4$H$_9$ | 90% |

[a]Reaction Conditions: 0.01 mmol catalyst and 1 mmol amine were heated in toluene under Argon flow.
[b]Determined by GC.

For the catalytic transfer hydrogenation of ketones or imines, a mixture containing ketone (0.5 mmol), ruthenium(II) complex (0.005 mmol) in 1 mL of 2-propanol in a schlenk flask equipped with a cooling finger are heated at the stated temperature (Table 3) under argon atmosphere. Thereafter, 0.1 mL of the reaction mixture was sampled and immediately diluted with 0.5-1.0 mL iPrOH for GC analysis. After the reaction was complete, the reaction mixture was condensed under reduced pressure and purified by silica gel column chromatography to afford the alcohol product.

TABLE 3

Transfer Hydrogenation of Ketones and Imines with Ru Complex.[a]

| Entry | Substrate | T (° C.) | Time | Yield (%)[b] |
|---|---|---|---|---|
| 1 | cyclohexanone | 40 | 24 h | >99 |
| 2 | acetophenone | 82 | 5 h | 90 |
| 3 | 2-hexanone | 40 | 24 h | 94 |
| 4 | 3-hexanone | 82 | 24 h | >99 |
| 5 | 4-heptanone | 82 | 24 h | >99 |
| 6 | N-benzylideneaniline | 40 | 24 h | 94 (92) |

[a]Reaction condition: 0.5 mmol of ketone, 1.0 mol % of Ru complex in 1 mL of $^i$PrOH;
[b]Determined by GC, isolated yield in parenthesis.

Example 2

Pd Complex Catalyzed Nigishi Coupling

Results for the cross-coupling reaction of two phenyl-based compounds are provided here. Under argon atmosphere, Pd complex 2 (2.3 mg, 0.005 mmol) and iodobenzene (102 mg, 0.5 mmol) were dissolved in THF. Then, the phenyl zinc chloride reagent (1 mmol) was added. The mixture was stirred overnight at 60° C.

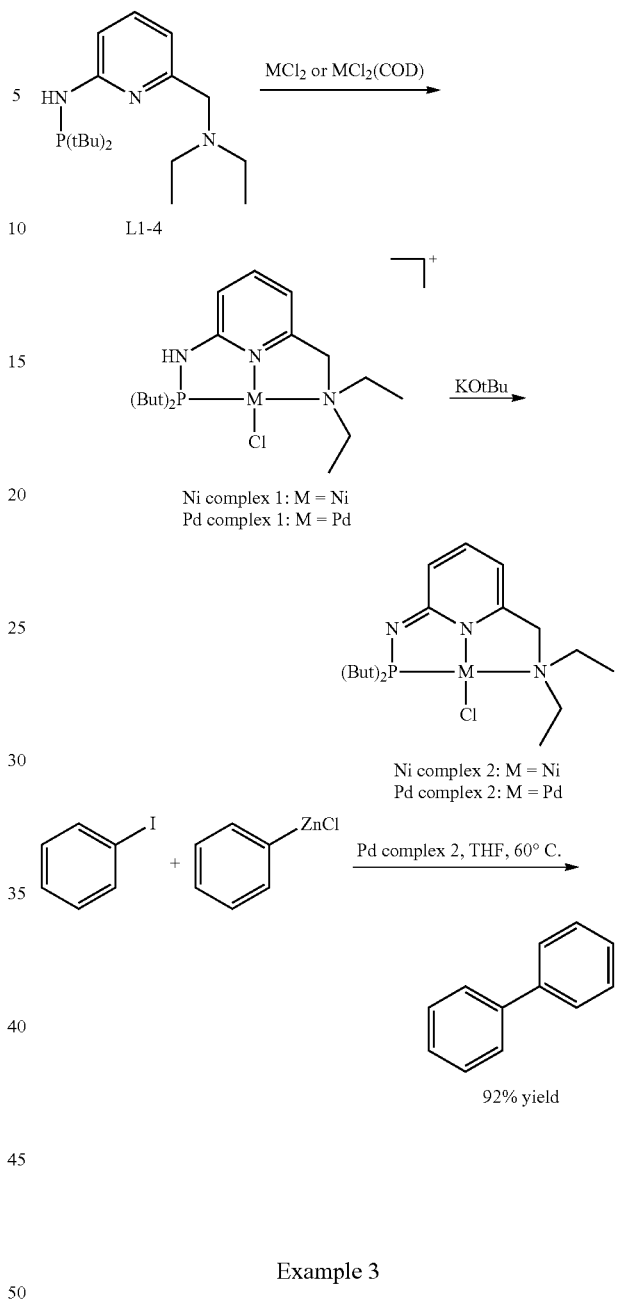

Example 3

Co Complex Catalyzed Butadiene Polymerization

Co complexes show high selectivity and activities in polymerization of butadiene to afford cis-1,4-polybutdiene materials. A representative procedure is as follows: A toluene solution of butadiene (1.62 g, 30 mmol) was added to a moisture free ampule bottle preloaded with the Co complex (10 μmol). MAO (Al, 2.0 mmol) was then injected to initiate the polymerization at 20° C. After 4 h, methanol was added to the system to quench the polymerization. The mixture was poured into a large quantity of methanol containing 2,6-di-tert-butyl-4-methylphenol (1.0 wt-%) as a stabilizer, then filtered and dried under vacuum at 40° C. The resulting polybutadiene was resulted had a constant weight.

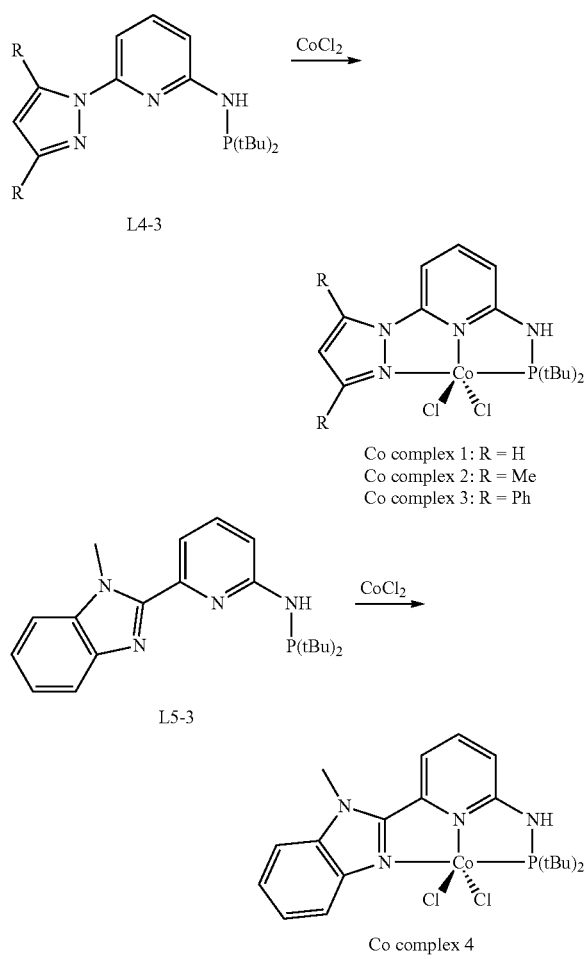

Co complex 1: R = H
Co complex 2: R = Me
Co complex 3: R = Ph

Co complex 4

TABLE 4

1,3-Butadiene Polymerization Results by Complexes 4a-4d/MAO.

| Complex | MAO/Co | M/Mt | Yield (%) | $M_n$ (×10$^{-4}$) | $M_w/M_n$ | Microstructure (%) | | |
|---|---|---|---|---|---|---|---|---|
| | | | | | | Cis-1,4 | Trans-1,4 | 1,2 |
| Co Complex 1 | 200 | 3000 | 99 | 12.6 | 2.2 | 98.2 | 0.3 | 1.5 |
| Co Complex 2 | 200 | 3000 | 99 | 13.5 | 2.0 | 98.7 | 0.2 | 1.1 |
| Co Complex 3 | 200 | 3000 | 95 | 15.9 | 1.5 | 99.6 | 0 | 0.4 |
| Co Complex 4 | 200 | 3000 | 91 | 14.2 | 1.8 | 98.9 | 0.1 | 1.0 |

Polymerization conditions: precursor, 10 μmol; butadiene: 25 wt-% in toluene, polymerization time 4 h; temperature, 20° C.

Example 4

Methods

All manipulation of air- and/or moisture-sensitive compounds were carried out under a dry argon atmosphere by using standard Schlenk techniques or under a dry argon atmosphere in an MBraun glovebox unless otherwise noted. All solvents were distilled under $N_2$ from appropriate drying agents. Deuterated solvents were dried with appropriate drying agents and distilled prior to use.

Column chromatography purifications were performed by flash chromatography using Merck silica gel 60. $^1$H, $^{13}$C and $^{31}$P NMR spectra were recorded using Bruker AMX-400 or AMX-500 NMR spectrometer. Chemical shifts were reported in parts per million (ppm), and the residual solvent peak was used as an internal reference: proton (benzene δ 7.16, chloroform δ 7.26). Multiplicity was indicated as follows: s (singlet), d (doublet), t (triplet), q (quartet), m (multiplet), dd (doublet of doublet), br s (broad singlet). Coupling constants were reported in Hertz (Hz). Mass spectra were recorded on Micromass Platform LCZ 4000, using Electro Spray Ionization (ESI) mode. The X-ray diffraction data were collected using Bruker-AXS KAPPA-APEXII CCD diffractometer. The yields of transfer hydrogenation products were determined by using Agilent 5975C inert XL EI/CI MSD with Triple-Axis Detector and crude $^1$H NMR.

Example 5

Ligand Synthesis

Schemes for synthesis of various classes of pincer ligands are shown in FIGS. 3-7.

Synthesis of N-(di-tert-butylphosphino)-6-((diethylamino)methyl)pyridin-2-amine L1-4

To a suspension of L1-3 (180 mg, 1 mmol) in toluene (10 ml) was added $NEt_3$ (0.24 mL, 2 mmol). The mixture was then cooled to 0° C., and $tBu_2PCl$ (180 mg, 1 mmol) was added dropwise. Upon further cooling to −70° C., n-BuLi (2 mmol, 1.25 mL of a 1.6 M solution in hexane) was slowly added. The solution was allowed to reach room temperature and was then stirred overnight at 80° C. After that, the solution was filtered the solvent was removed under vacuum to afford the crude product L1-4, which was used for next step without further purification.

Synthesis of 6-bromo-N-(1-hydroxy-2-methylpropan-2-yl)picolinamide L2-1

To a solution of oxalyl chloride (7.5 mmol, 635 μL) in THF (10 mL) were added 2-bromo-pyridine-6-carboxylic acid (5.0 mmol, 1.01 g), and the reaction mixture was stirred for 1 hour at room temperature. The excess oxalyl chloride and the solvent were removed under reduced pressure, and the solid residue was dissolved in $CH_2Cl_2$ (20 mL). This solution was added dropwise to a cooled solution of 2-amino-2-methyl-1-propanol (6.0 mmol, 618 mg) and triethylamine (9.0 mmol, 1.2 mL) in $CH_2Cl_2$ (20 mL). The solution was stirred for 4 h, and then quenched with 1 M NaOH (50 mL). The organic layer was separated, washed with saturated $NaHCO_3$, brine and dried over $MgSO_4$. The crude product was purified by column chromatography on silica gel (Hexanes:ethyl acetate=2:1 as eluent) to afford white solid (1.10 g, 81%). $^1$H NMR (400 MHz, $CDCl_3$): 8.14 (d, 1H, J=7.6 Hz), 7.91 (br, 1H), 7.72 (t, 1H, J=7.8 Hz), 7.62 (d, 1H, J=7.9 Hz), 4.65 (t, 1H, J=6.4 Hz), 3.73 (d, 2H, J=6.4 Hz), 1.43 (s, 6H). $^{13}$C NMR (100 MHz, $CDCl_3$): 163.07, 150.96, 140.36, 139.75, 130.82, 121.14, 70.44, 56.24, 24.68. MS (ESI, MeOH): 273 (100%, $(M+1)^+$).

Synthesis of 6-amino-N-(1-hydroxy-2-methylpropan-2-yl)picolinamide L2-2

A mixture of 6-bromo-N-(1-hydroxy-2-methylpropan-2-yl)picolinamide (0.5 mmol, 136 mg), 3 mL of 37% NH3.H2O and 32 mg (0.5 mmol) of copper powder in 3 mL iPrOH was heated at 100° C. in sealed tube for 24 hours. After cooling to room temperature, brine was added and the mixture was extracted with DCM (20 mL×3). The combined organic layers were washed with brine, dried over MgSO4. After solvent evaporation, the crude product was crystallized from ethyl acetate to obtain compound 2 as a white solid (75 mg, 72%). $^1$H NMR (500 MHz, CDCl$_3$): 8.04 (br, 1H), 7.59-7.56 (m, 1H), 7.54-7.52 (m, 1H), 6.64 (d, 1H, J=8.9 Hz), 5.24 (t, 1H, J=6.4 Hz), 4.52 (br, 2H), 3.70 (d, 2H, J=6.4), 1.40 (s, 6H). $^{13}$C NMR (125 MHz, CDCl$_3$): 164.99, 156.79, 147.91, 139.01, 112.66, 111.82, 70.93, 55.90, 24.85. MS (ESI, MeOH): 210 (40%, (M+1)), 441 (100%, (M+23)).

Synthesis of 6-amino-N-(1-chloro-2-methylpropan-2-yl)picolinamide L2-3

A solution of 6-amino-N-(1-hydroxy-2-methylpropan-2-yl)picolinamide (0.35 mmol, 74 mg) in CHCl$_3$ was cooled to 0° C. and SOCl$_2$ (2.8 mmol, 200 μL) was added. The mixture was refluxed overnight. After cooling to room temperature, the reaction was quenched with 1 M NaOH. The aqueous phase was extracted with CH$_2$Cl$_2$, and the combined organic phases were dried with MgSO$_4$. The crude product was purified by column chromatography on silica gel (Hexanes:ethyl acetate=2:1 as eluent). White solid, 76 mg, 95% yield. $^1$H NMR (500 MHz, CDCl$_3$): 7.93 (br, 1H), 7.57-7.54 (m, 1H), 7.52-7.51 (m, 1H), 6.62 (d, 1H, J=8.0 Hz), 4.51 (br, 2H), 3.94 (s, 2H), 1.52 (s, 6H). $^{13}$C NMR (125 MHz, CDCl$_3$): 163.97, 156.83, 148.37, 138.88, 112.33, 111.63, 53.72, 51.19, 25.08. MS (ESI, MeOH): 228 (100%, (M+1)$^+$).

Synthesis of 6-(4,4-dimethyl-4,5-dihydrooxazol-2-yl)pyridin-2-amine L2-4

To a suspension of sodium hydride (633 mg, 27.5 mmol) in THF (40 mL) at 0° C., 6-amino-N-(1-chloro-2-methylpropan-2-yl)picolinamide in 10 mL (1.10 g, 4.82 mmol) was added dropwise and the mixture was stirred at 0° C. for 3 hours. The reaction was quenched with water. The aqueous phase was extracted with CH$_2$Cl$_2$, and the combined organic phases were dried with MgSO$_4$. The crude product was crystallized from ethyl acetate/hexanes to obtain compound 4 as a white solid (746 mg, 81%). $^1$H NMR (500 MHz, CDCl$_3$): 7.48 (t, 1H, J=7.6 Hz), 7.35 (d, 1H, J=7.4 Hz), 6.58 (d, 1H, J=8.2 Hz), 4.64 (br, 2H), 4.14 (s, 2H), 1.40 (s, 6H). $^{13}$C NMR (125 MHz, CDCl$_3$): 161.35, 158.17, 145.06, 138.06, 114.30, 111.07, 79.44, 67.75, 28.38. MS (ESI, MeOH): 192 (100%, (M+1)$^+$).

Synthesis of N-(di-tert-butylphosphino)-6-(4,4-dimethyl-4,5-dihydrooxazol-2-yl)pyridin-2-amine L2-5

To a suspension of 6-(4,4-dimethyl-4,5-dihydrooxazol-2-yl)pyridin-2-amine (95 mg, 0.5 mmol) in toluene was added NEt$_3$ (70 μL, 0.5 mmol). The mixture was then cooled to 0° C., and (tBu)$_2$PCl (96 μL, 0.5 mmol) was added dropwise. Upon further cooling to −70° C., n-BuLi (0.5 mmol, 320 μL of a 1.6 M solution in hexane) was slowly added. The solution was allowed to reach room temperature and was then stirred overnight at 80° C. After that, the solution was filtered and the solvent was removed under vacuum. The remaining yellow oil was washed with hexanes. The resulting product (with a purity of 80% as determined by NMR spectroscopy) was directly used for the next step. $^{31}$P NMR (162 MHz, CDCl$_3$): δ5.93 (s). MS (ESI, MeOH): 336 (100%, (M+1)$^+$).

Synthesis of [2,2'-bipyridin]-6-amine L3-1

To a mixture of 6-bromo-2,2'-bipyridine (3.0 mmol, 705 mg) and Cu$_2$O (0.01 mmol, 1.0 mg) in glycol in autoclave NH$_3$ was feed. The reaction was maintained under 10 atm of NH$_3$ at 110° C. for 24 h. After cooling to room temperature, water was added and the aqueous phase was extracted with DCM. The combined organic layers were washed with brine and dried over MgSO$_4$. After solvent evaporation, the crude product was purified by column chromatography on silica gel (Hexanes:ethyl acetate=1:1 as eluent) to afford a white solid (437 mg, 85% yield). $^1$H NMR (500 MHz, CDCl$_3$, ppm): 8.65 (s, 1H), 8.25 (d, 1H, J=7.9 Hz), 7.79-7.76 (m, 1H), 7.71-7.70 (m, 1H), 7.57 (t, 1H, J=7.1 Hz), 7.26 (t, 1H, J=7.1 Hz), 6.65 (d, 1H, J=7.9 Hz), 4.53 (br, 2H). $^{13}$C NMR (125 MHz, CDCl$_3$, ppm): 157.97, 156.38, 154.57, 149.11, 138.58, 136.73, 123.31, 120.94, 111.59, 108.87.

Synthesis of 2-bromo-6-(1H-pyrazol-1-yl)pyridine L4-1-1

To a solution of 1H-Pyrazole (10.0 mmol, 680 mg) in distilled dioxane (30 mL) were added KOtBu (11.0 mmol, 1.26 g), and followed by addition of 2,6-dibromopyridine (10.0 mmol, 2.37 g). The reaction mixture was refluxed for 48 hour, and then quenched with 5 mL of water. Solvent was removed under reduced pressure and water was added to the residue, then the mixture was extracted with DCM. The combined organic layers were washed with brine and dried over MgSO$_4$. After solvent evaporation, the crude product was purified by column chromatography on silica gel (Hexanes:ethyl acetate=20:1 as eluent) to afford a white solid (2.01 g, 90%). $^1$H NMR (400 MHz, CDCl$_3$, ppm): 8.53 (s, 1H), 7.92 (d, 1H, J=7.6 Hz), 7.73 (s, 1H), 7.67 (t, 1H, J=7.8 Hz), 7.35 (d, 1H, 7.6 Hz), 6.46 (s, 1H). $^{13}$C NMR (100 MHz, CDCl$_3$, ppm): 162.72, 140.73, 139.91, 127.58, 125.25, 110.89, 108.23.

Compounds L4-1-2 and L4-1-3 were obtained with the same procedure as compound L4-1-1.

L4-1-2

$^1$H NMR (400 MHz, CDCl$_3$, ppm): 7.90 (d, 1H, J=7.6 Hz), 7.55 (d, 1H, J=7.6 Hz), 7.25 (t, 1H, J=7.8 Hz), 6.96 (s, 1H), 2.61 (s, 3H), 2.24 (s, 3H). $^{13}$C NMR (100 MHz, CDCl$_3$, ppm): 153.15, 150.53, 142.21, 140.25, 138.87, 124.20, 113.50, 109.74, 14.73, 13.68.

L4-1-3

$^1$H NMR (400 MHz, CDCl$_3$, ppm): 7.96 (d, 2H, J=7.6 Hz), 7.46 (d, 1H, J=7.6 Hz), 7.44 (t, 1H, J=7.8 Hz), 7.39-7.26 (m, 9H), 6.82 (s, 1H). $^{13}$C NMR (100 MHz, CDCl$_3$): 152.55, 151.68, 145.28, 139.76, 139.06, 132.09, 128.64, 128.33, 128.11, 128.03, 127.71, 126.70, 125.78, 125.65, 115.94, 106.83.

Synthesis of 2-Amino-6-(1H-pyrazol-1-yl)pyridine L4-2-1

To a mixture of 2-bromo-6-(1H-pyrazol-1-yl)pyridine (3.0 mmol, 669 mg) and Cu$_2$O (0.01 mmol, 1.0 mg) in glycol in autoclave NH$_3$ was feed. The reaction was maintained under 10 atm of NH$_3$ at 110° C. for 24 h. After cooling to room temperature, water was added and the aqueous phase was extracted with DCM. The combined organic layers were washed with brine and dried over MgSO$_4$. After solvent evaporation, the crude product was purified by column chromatography on silica gel (Hexanes:ethyl acetate=6:1 as eluent) to afford a white solid (388 mg, 81% yield). $^1$H NMR (400 MHz, CDCl$_3$, ppm): 8.44 (s, 1H), 7.69 (s, 1H), 7.53 (m, 1H), 7.28 (m, 1H), 6.42-6.37 (m, 2H), 4.49 (br, 2H). $^{13}$C NMR (100 MHz, CDCl$_3$, ppm): 151.45, 142.72, 140.73, 139.91, 127.58, 125.25, 110.89, 108.23.

Compounds L4-2-2 and L4-2-3 were obtained with the same procedure as compound L4-2-1.

L4-2-2

$^1$H NMR (400 MHz, CDCl$_3$, ppm): 7.50 (t, 1H, 7.60 Hz), 7.06 (d, 1H, 7.60 Hz), 6.64 (d, 1H, 6.80 Hz), 5.95 (s, 1H), 4.42 (br, 2H), 2.55 (s, 3H), 2.28 (s, 3H). $^{13}$C NMR (100 MHz, CDCl$_3$, ppm): 157.07, 152.09, 149.40, 140.97, 139.79, 108.42, 105.82, 105.29.

L4-2-3

$^1$H NMR (400 MHz, CDCl$_3$, ppm): 7.37 (d, 2H, 7.60 Hz), 7.33-7.31 (m, 9H), 6.81 (s, 1H), 6.41 (s, 1H), 4.41 (br, 2H). $^{13}$C NMR (100 MHz, CDCl$_3$, ppm): 159.6, 151.51, 150.74, 146.35, 138.82, 133.14, 131.44, 129.5, 128.7, 127.8, 107.24, 103.48.

Synthesis of N-(di-tert-butylphosphino)-6-(1H-pyrazol-1-yl)pyridine L4-3-1

To a suspension of 2-Amino-6-(1H-pyrazol-1-yl)pyridine (320 mg, 2.0 mmol) in toluene (30 mL) was added NEt$_3$ (0.27 mL, 2.0 mmol). The mixture was then cooled to 0° C., and (tBu)$_2$PCl (0.39 mL, 2.0 mmol) was added dropwise. Upon further cooling to −70° C., n-BuLi (2.0 mmol, 1.28 mL of a 1.6 M solution in hexane) was slowly added. The solution was allowed to reach room temperature and was then stirred overnight at 80° C. After that, the solution was filtered and the solvent was removed under vacuum. The remaining yellow oil was purified by column chromatography on silica gel (Hexanes:ethyl acetate=15:1 as eluent) to afford a white solid (550 mg, 91% yield). $^{31}$P NMR (162 MHz, CDCl$_3$, ppm): 59.76 (s). $^1$H NMR (400 MHz, CDCl$_3$, ppm): 8.46 (s, 1H), 7.68 (s, 1H), 7.54 (t, 2H, J=7.6 Hz), 7.03 (d, 1H, J=7.8 Hz), 6.40 (s, 1H), 4.95 (d, 1H, 10.8 Hz), 1.18 (s, 9H), 1.14 (s, 9H). $^{13}$C NMR (100 MHz, CDCl$_3$, ppm): 150.49, 147.71, 141.42, 137.96, 136.59, 137.04, 122.60, 122.01, 119.61, 115.21, 109.34, 109.16, 33.80, 33, 65, 32.16, 27.76, 27.64.

Compounds L4-3-2, L4-3-3 were obtained with the same procedure as compound L4-3-1.

L4-3-2

$^{31}$P NMR (162 MHz, CDCl$_3$, ppm): 59.97 (s). $^1$H NMR (400 MHz, CDCl$_3$, ppm): 7.52 (t, 1H, 7.6 Hz), 7.03 (d, 1H, J=7.6 Hz), 6.97 (d, 1H, J=7.6 Hz), 4.95 (d, 1H, 10.4 Hz), 2.53 (s, 3H), 2.28 (s, 3H), 1.16 (s, 9H), 1.13 (s, 9H). $^{13}$C NMR (100 MHz, CDCl$_3$, ppm): 161.71, 148.0, 144.3, 140.71, 139.55, 108.23, 106.41, 106.22, 34.21, 34.01, 28.16, 28.00, 14.03, 13.69.

L4-3-3

$^{31}$P NMR (162 MHz, CDCl$_3$, ppm): 59.96 (s). $^1$H NMR (400 MHz, CDCl$_3$, ppm): 7.92 (d, 2H, 7.6 Hz), 7.34 (d, 2H, J=7.6 Hz), 7.33 (d, 2H, J=7.6 Hz), 7.31-7.27 (m, 5H), 7.08 (d, 1H, 7.2 Hz), 6.86 (d, 1H, 7.2 Hz), 4.73 (d, 1H, 10.8 Hz), 1.09 (s, 9H), 1.06 (s, 9H). $^{13}$C NMR (100 MHz, CDCl$_3$, ppm): 160.37, 160.15, 152.18, 150.78, 148.0, 144.93, 139.56, 133.07, 131.59, 128.80, 128.60, 128.03, 127.88, 126.05, 108.55, 107.62, 107.42, 105.67, 34.20, 34.01, 29.74, 28.06, 27.91.

Synthesis of 2-(6-Bromopyridin-2-yl)-1H-benzimidazole L5-1

The mixture of 6-Bromopyridine-2-carboxylic acid (2.01 g, 10 mmol) and benzene-1,2-diamine (1.08, 10 mmol) in polyphosphoric acid was heated at 220° C. for 4 h. The solution was poured into ice-water, and the formed precipitate was collected by filtration and further washed with NaHCO$_3$ and water. After recrystallization in ethanol, the desired product was obtained in yield of 65% (1.76 g). $^1$H NMR (400 MHz, CDCl$_3$, ppm): 8.31 (d, 2H, J=7.2 Hz), 8.03 (t, 1H, J=7.6 Hz), 7.63 (m, 2H), 7.24 (s, 2H). $^{13}$C NMR (100 MHz, CDCl$_3$): 150.20, 148.63, 142.46, 139.46, 135.32, 129.87, 128.04, 124.30, 123.29, 122.92, 120.21, 110.09.

Synthesis of 2-(6-Aminopyridin-2-yl)-1-methylbenzimidazole L5-2

To a solution of 2-(6-Bromopyridin-2-yl)-1H-benzimidazole (1.36 g, 5 mmol) in acetone (30 mL), KOH powder (1.12 g, 20 mmol) was added. After stirred for 30 min, iodomethane (20 mmol, 0.87 mL) was added dropwise at 0° C., and the mixture was stirred at room temperature overnight. The solution was poured into ice-water and white precipitate formed, which was filtered and washed with water. After crystallization from methanol, the obtained compound was ammonized with the same procedure as 1d (90.1 mg, 81%).

$^1$H NMR (400 MHz, CDCl$_3$, ppm): 7.82 (d, 2H, J=7.6 Hz), 7.46 (d, 2H, J=7.69 Hz), 7.60 (t, 2H, J=7.8 Hz), 7.43-7.26 (m, 7H), 6.65 (d, 2H, 7.6 Hz), 4.31 (s, 3H). $^{13}$C NMR (100 MHz, CDCl$_3$, ppm): 157.49, 150.71, 148.52, 142.23, 138.59, 137.04, 123.15, 122.59, 119.90, 115.45, 109.81, 108.98, 32.63.

Synthesis of L5-3

Compounds L5-3 were obtained with the same procedure as compound L4-3. $^{31}$P NMR (162 MHz, CDCl$_3$, ppm): 60.34 (s). $^1$H NMR (400 MHz, CDCl$_3$, ppm): 7.62 (d, 1H, J=7.6 Hz), 7.41 (t, 2H, J=7.6 Hz), 7.33 (d, 1H, J=7.8 Hz), 7.31-7.26 (m, 2H), 7.18 (d, 2H, 7.6 Hz), 5.03 (d, 1H, 6.6 Hz), 4.21 (s, 3H). $^{13}$C NMR (100 MHz, CDCl$_3$, ppm): 150.49, 147.71, 141.42, 137.96, 136.59, 137.04, 122.60, 122.01, 119.61, 115.21, 109.34, 109.16, 33.80, 33, 65, 32.16, 27.76, 27.64.

Example 6

Transition Metal Complex Synthesis

Synthesis of Ru Complex 1

L1-4 was dissolved in THF (10 mL) and RuHCl(PPh$_3$)$_3$(CO) (953 mg, 1 mmol) was added. The mixture was stirred and heated at 65° C. for 12 hrs, then cooled to room temperature. The pale yellow solid obtained was filtered and washed with ether (3×3 mL), then dried under vacuum (270 mg, 55%). ESI-MS (m/z): 454.28 (100%, (M-Cl)). $^{31}$P {$^1$H}

NMR (CDCl$_3$): 162.3 (s). $^1$H NMR (CDCl$_3$): −15.96 (d, 1H, J=28.6 Hz), 1.15-1.22 (m, 3H), 1.25-1.32 (m, 3H), 1.33-1.41 (m, 9H), 1.45-1.41 (m, 9H), 2.74-2.83 (m, 2H), 3.53-3.65 (m, 2H), 3.80-3.92 (m, 1H), 5.06 (d, 1H, J=14.2 Hz), 5.31 (br, 1H), 6.71-6.73 (m, 2H), 6.46-6.48 (m, 1H).

Synthesis of Ru Complex 2

To a suspension of complex 6 (49 mg, 0.1 mmol) in THF (5 mL) was added tBuOK (11.2 mg, 0.1 mmol) and the mixture was stirred at room temperature for 30 min and then filtered. The gray filtrate was concentrated under vacuum to 0.5 mL and 5 mL pentane was added to precipitate a gray solid, which was filtered and washed with pentane (3×2 mL), then dried under vacuum (37 mg, 82%). ESI-MS (m/z): 454.33 (100, (M+1)$^+$). $^{31}$P{$^1$H} NMR (C$_6$D$_6$): 144.2. $^1$H NMR (C$_6$D$_6$): −26.2 (d, 1H, J=25.7 Hz), 0.59-0.61 (m, 3H), 0.86-0.90 (m, 3H), 1.41-1.48 (m, 18H), 1.90-2.01 (m, 1H), 2.11-2.21 (m, 1H), 2.28-2.33 (m, 1H), 2.57-2.68 (m, 1H), 2.74 (d, 1H, J=14.4 Hz), 3.56 (d, 1H, J=14.4 Hz), 5.57 (d, J=6.5 Hz, 1H), 6.80-6.87 (m, 1H), 6.93-6.97 (m, 1H).

Synthesis of Ru Complex 3

To an oven dried 25 mL pressure vessel equipped with magnetic stirring bar was added ligand L2-5 (168 mg, 0.5 mmol), RuHCl(CO)(PPh$_3$)$_3$ (476 mg, 0.5 mmol), and 10 mL dry THF in a Argon glove box. The flask was sealed and heated at 68° C. overnight with stirring outside the glove box, then cooled to room temperature to lead to reddish-brown solid. Filtered and the solid thus obtained was washed with pentane (3×5 mL), then dried under vacuum to give pure complex 6 (163 mg, 65%). $^{31}$P NMR (162 MHz, CD$_2$Cl$_2$): 162.57 (s). $^1$H NMR (500 MHz, CD$_2$Cl$_2$): 7.56 (t, 1H, J=7.9 Hz), 7.11 (d, 1H, J=7.4 Hz), 6.28 (br, 1H), 5.31 (m, 1H), 4.46 (dd, 2H, J=23.4 Hz and 8.4 Hz), 1.64 (s, 3H), 1.42 (s, 3H), 1.39 (d, 9H, J=14.6 Hz), 1.25 (d, 9H, J=14.6 Hz), −16.58 (d, 1H, J=19.8 Hz). $^{13}$C NMR (125 MHz, CD$_2$Cl$_2$): 207.81, 163.20, 161.00, 144.35, 138.23, 114.82, 111.84, 81.99, 68.17, 41.16 (d, J=14 Hz), 39.21 (d, J=24 Hz), 30.35 (d, J=5.7 Hz), 29.18 (d, J=4.6), 28.62, 28.04. MS (ESI, MeOH): 466 (100%, (M-Cl)$^+$). The crystal suitable for a single-crystal X-ray diffraction was obtained from CH$_2$Cl$_2$/n-Pentane.

Synthesis of Ru Complex 4

To a suspension of Ru complex 3 (50 mg, 0.1 mmol) in dry THF (4 mL) in a argon glove box was added KOtBu (11.2 mg, 0.1 mmol) and the mixture was stirred for 5 minutes and the solvent was removed under vacuum. The product was extracted using n-pentane (3×5 mL) and passed through celite. The resulting solution was concentrated to afford a dark-red solid (45.1 mg, 97%). $^{31}$P NMR (162 MHz, C$_6$D$_6$): 148.01 (s). $^1$H NMR (500 MHz, C$_6$D$_6$): 7.05 (d, 1H, J=11.3 Hz), 6.61 (t, 1H, J=11.1 Hz), 6.25 (d, 1H, J=8.1 Hz), 3.49 (d, 1H, J=8.5 Hz), 3.40 (d, 1H, J=8.5 Hz), 1.38 (t, 18H, J=12.7), 0.96 (d, 6H, J=2.6 Hz), −26.83 (br, 1H). $^{13}$C NMR (125 MHz, C$_6$D$_6$): 207.53 (d, J=28 Hz), 170.45, 168.89, 142.67, 134.95, 120.87, 120.50, 105.94, 79.83, 65.34, 42.48 (d, J=46.9 Hz), 35.82 (d, J=54.7 Hz), 28.42, 27.48, 27.11, 26.80. MS (ESI, MeOH): 466 (100%, (M+1)).

Compounds L3-2 and Ru complex 5 and 6 were obtained with the same procedures as compound L2-5, Ru complex 3 and 4.

L3-2

$^1$H NMR (400 MHz, CDCl$_3$, ppm): 8.66 (s, 1H), 8.26 (d, 1H, J=7.9 Hz), 7.80-7.76 (m, 1H), 7.68-7.66 (m, 1H), 7.61-7.57 (m, 1H), 7.26 (m, 1H), 5.11 (d, 1H, J=7.9 Hz), 4.67 (br, 2H). $^{31}$P NMR (162 MHz, CDCl$_3$, ppm): 59.61.

Ru Complex 5

$^1$H NMR (500 MHz, CD$_3$OD, ppm): 9.05 (s, 1H), 8.26 (d, 1H, J=7.9 Hz), 8.05-8.03 (m, 1H), 7.81-7.79 (m, 1H), 7.70-7.68 (m, 1H), 7.58-7.12 (m, 1H), 7.11 (d, 1H, J=8.4 Hz), 1.38 (d, 9H, J=14.5 Hz), 1.26 (d, 9H, J=14.5), −18.71 (d, 1H, J=23.6 Hz).

Ru Complex 6

$^{31}$P NMR (162 MHz, C$_6$D$_6$, ppm): 140.83 (d, J=20.3 Hz). $^1$H NMR (400 MHz, C$_6$D$_6$, ppm): 8.50 (s, 1H), 7.07 (d, 1H, J=8.9 Hz), 6.77-6.75 (m, 2H), 7.66-7.62 (m, 1H), 6.16 (t, 1H, J=5.8), 6.03 (d, 1H, J=7.0), 1.43 (d, 9H, J=14.5 Hz), 1.38 (d, 9H, J=14.5), −25.37 (d, 1H, J=23.6 Hz). $^{13}$C NMR (100 MHz, C$_6$D$_6$, ppm): 207.54, 171.32, 161.25, 153.03, 136.25, 135.96, 123.93, 120.65, 118.86, 118.65, 103.58 42.69 (d, J=26.5). 36.43 (d, J=26.5), 28.87, 28.15.

Synthesis of Pd Complex 1

To a suspension of L1-4 (180 mg, 1 mmol) in toluene (10 mL) was added NEt$_3$ (0.24 mL, 2 mmol). The mixture was then cooled to 0° C., and tBu$_2$PCl (180 mg, 1 mmol) was added dropwise. Upon further cooling to −78° C., n-BuLi (2 mmol, 1.25 mL of a 1.6 M solution in hexane) was slowly added. The solution was allowed to reach room temperature and was then stirred overnight at 80° C. After that, the solution was filtered the solvent was removed under vacuum. The remaining yellow oil was then dissolved in toluene (10 mL) and PdCl$_2$(COD) (285 mg, 1 mmol) was added. The mixture was stirred and heated at 100° C. for 12 hrs, then cooled to room temperature. The pale yellow solid Ni complex 1 thus obtained was filtered and washed with ether (3×3 mL), then dried under vacuum (325 mg, 55%). $^{31}$P{$^1$H} NMR (CDCl$_3$): 138.2. $^1$H NMR (400 MHz, CDCl$_3$): 1.58 (t, 6H, J=7.12 Hz), 1.62 (s, 9H), 1.66 (s, 9H), 2.77-2.87 (m, 2H), 3.32-3.40 (m, 2H), 4.22 (s, 2H), 6.78 (d, 1H, J=7.32 Hz), 7.66 (dd, 1H, J$_1$=7.32 Hz, J$_2$=8.52 Hz), 8.06 (d, 1H, J=8.52 Hz), 11.20 (s, 1H).

Synthesis of Pd Complex 2

To a suspension of Ni complex 1 (75 mg, 0.15 mmol) in THF (5 ml) was added t-BuOK (19 mg, 0.165 mmol), The solution immediately changed to clear yellow color. The mixture was stirred at room temperature for 3 h and then filtered. The yellow filtrate was concentrated under vacuum to 0.5 mL and 5 mL pentane was added to precipitate a red orange solid, which was filtered and washed with pentane (3×2 mL), then dried under vacuum (55 mg, 80%). $^{31}$P{$^1$H} NMR (C$_6$D$_6$): 132.6. $^1$H NMR (400 MHz, C$_6$D$_6$): 1.21 (t, 6H, J=7.12 Hz), 1.56 (s, 9H), 1.60 (s, 9H), 2.06-2.15 (m, 2H), 2.78-2.86 (m, 2H), 3.12 (s, 2H), 5.47 (d, 1H, J=5.24 Hz), 6.4-6.78 (m, 2H).

Synthesis of Ni complex 1

The synthetic procedure of Ni complex 1 is the same as Pd complex 1. $^{31}$P{$^1$H} NMR (CDCl$_3$): 118.6. $^1$H NMR (400 MHz, CDCl$_3$): 1.71 (s, 9H), 1.75 (s, 9H), 1.90 (t, 6H, J=7.08 Hz), 2.49-2.55 (m, 2H), 3.24-3.32 (m, 2H), 3.98 (s, 2H), 6.55 (d, 1H, J=7.20 Hz), 7.57 (dd, 1H, J$_1$=7.20 Hz, J$_2$=8.52 Hz), 7.90 (d, 1H, J=8.52 Hz), 10.94 (s, 1H).

Synthesis of Ni complex 2

The synthetic procedure of Ni complex 2 is the same as Pd complex 2. $^{31}P\{^1H\}$ NMR (CDCl$_3$): 119.2. $^1$H NMR (400 MHz, CDCl$_3$): 1.55 (s, 9H), 1.60 (s, 9H), 1.86 (t, 6H, J=7.12 Hz), 2.38-2.47 (m, 2H), 3.13-3.21 (m, 2H), 3.81 (s, 2H), 5.78 (d, 1H, J=6.76 Hz), 6.37 (d, 1H, J=8.76 Hz), 7.01 (dd, 1H, J$_1$=6.76 Hz, J$_2$=8.76 Hz).

Synthesis of Co Complex 1

To a suspension of CoCl$_2$ (127 mg, 1.0 mmol) in THF (10 mL), a solution of N-(di-tert-butylphosphino)-6-(1H-pyrazol-1-yl)pyridine (304 mg, 1.0 mmol) in THF (5 mL) was added dropwise. The mixture was stirred at room temperature 24 h. Diethyl ether (10 mL) was added and the precipitate formed, which was filtered and washed with heptane. Dried at vacuum overnight at 30° C., product was finally obtained (404 mg, 93% yield). Anal. Calcd. for C$_8$H$_7$N$_2$CoCl$_2$N$_4$: C, 33.25; H, 2.44; N, 19.34. Found: C, 34.06; H, 2.53; N, 19.81. MS (ESI, DCM): 289 (100%, (M+1)$^+$), 311 (96%, (M+23)$^+$).

Co complexes 2 and 3 were obtained with the same procedure as Co complex 1:

Co Complex 2

Anal. Calcd. for C$_{10}$H$_{11}$N$_2$CoCl$_2$N$_4$: C, 37.88; H, 3.50; N, 17.67. Found: C, 38.09; H, 3.57; N, 16.94. MS (ESI, DCM): 317 (85%, (M+1)), 339 (100%, (M+23)$^+$).

Co Complex 3

Anal. Calcd. for C$_{20}$H$_{15}$N$_2$CoCl$_2$N$_4$: C, 54.45; H, 3.43; N, 12.70. Found: C, 54.19; H, 3.51; N, 12.90. MS (ESI, DCM): 441 (100%, (M+1)), 464 (20%, (M+23)$^+$).

Synthesis of Co Complex 4

Co complex 4 was obtained with the same procedure as Co complex 1. Anal. Calcd. for C$_{20}$H$_{15}$N$_2$CoCl$_2$N$_4$: C, 44.22; H, 3.14; N, 15.87. Found: C, 44.10; H, 3.50; N, 15.96. MS (ESI, DCM): 353 (100%, (M+1)$^+$), 375 (20%, (M+23)$^+$).

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Bordwell, Chem. Res., 21:456, 1988.
Gnanaprakasam and Milstein, J. Am. Chem. Soc., 133:1682, 2011.
Gnanaprakasam et al., Adv. Synth. Catal., 352:3169, 2010.
Goldman et al., Science, 312:257, 2006.
Gunanathan et al., J. Am. Chem. Soc., 132:14763, 2010.
Gunanathan et al., Science, 317:790, 2007.
Gupta et al., Chem. Commun., 2083, 1996.
Gupta et al., Chem. Commun., 461, 1997.
Gupta et al., J. Am. Chem. Soc., 119:840, 1997.
Haenel et al., Angew. Chem. Int. Ed., 40:3596, 2001.
Jensen, In: The Chemistry of Pincer Compounds Morales-Morales, Elsevier Science 2007.
Joule and Mills, In: Heterocyclic Chemistry; 5$^{th}$ Ed., John Wiley & Sons Ltd., West Sussex, 2010.
Langer et al., Angew. Chem. Int. Ed., 50:2120, 2011.
Liu et al., J. Am. Chem. Soc., 121:4086, 1999.
March's Advanced Organic Chemistry: Reactions, Mechanisms, and Structure, 2007.
Milstein et al., US 2009/0112005 A1, 2008.
Milstein, Top. Catal., 53:915, 2010.
Practical Process Research & Development, 2000.
Ray et al., Chem. Commun., 3388, 2005.
Tanaka et al., J. Am. Chem. Soc., 131:14168, 2009.
van der Boom and Milstein, Chem. Rev., 103:1759, 2003.
Xu et al., Chem. Commun., 2273, 1997.

The invention claimed is:

1. A compound of the formula:

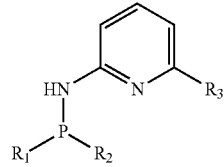

(I)

wherein:
R$_1$ and R$_2$ are each independently alkyl$_{(C \leq 12)}$, aryl$_{(C \leq 12)}$, aralkyl$_{(C \leq 12)}$, or a substituted version of any of these groups; and
R$_3$ is a group comprising a nitrogen atom that is separated by one atom from the carbon atom to which R$_3$ is connected.

2. The compound of claim 1, wherein R$_1$ and R$_2$ are each tert-butyl.

3. The compound of claim 1, wherein R$_3$ is selected from the group consisting of formulas:

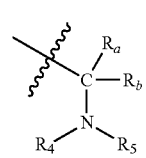

(a)

wherein:
R$_a$ and R$_b$ are each independently hydrogen or fluoro; and
R$_4$ and R$_5$ are each independently alkyl$_{(C \leq 8)}$, aryl$_{(C \leq 8)}$, aralkyl$_{(C \leq 8)}$, or a substituted version of any of these groups;

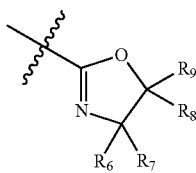

wherein:
 $R_6$, $R_7$, $R_8$ and $R_9$ are each independently:
  hydrogen; or
  alkyl$_{(C\leq 8)}$, aryl$_{(C\leq 8)}$, aralkyl$_{(C\leq 8)}$, or a substituted version of any of these groups;

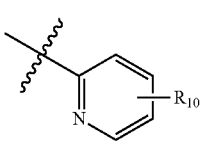

wherein:
 $R_{10}$ is:
  hydrogen, hydroxy, amino, halo, nitro; or
  alkyl$_{(C\leq 8)}$, alkoxy$_{(C\leq 8)}$, alkylamino$_{(C\leq 8)}$, dialkylamino$_{(C\leq 8)}$, or a substituted version of any of these groups;

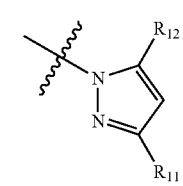

wherein:
 $R_{11}$ and $R_{12}$ are each independently:
  hydrogen; or
  alkyl$_{(C\leq 8)}$, aryl$_{(C\leq 8)}$, aralkyl$_{(C\leq 8)}$, or a substituted version of any of these groups; and

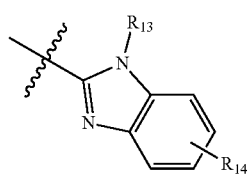

wherein:
 $R_{13}$ is hydrogen, alkyl$_{(C\leq 8)}$ or substituted alkyl$_{(C\leq 8)}$; and
 $R_{14}$ is:
  hydrogen, hydroxy, amino, halo, nitro; or
  alkyl$_{(C\leq 8)}$, alkoxy$_{(C\leq 8)}$, alkylamino$_{(C\leq 8)}$, dialkylamino$_{(C\leq 8)}$, or a substituted version of any of these groups;
and a salt or tautomer thereof.

4. The compound of claim 1, wherein $R_3$ is formula (a).
5. The compound of claim 4, wherein $R_a$ and $R_b$ are hydrogen.
6. The compound of claim 4, wherein $R_4$ and $R_5$ are each alkyl$_{(C\leq 8)}$.

7. The compound of claim 6, further defined as:

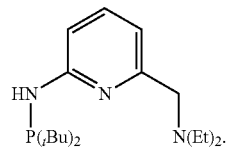

8. The compound of claim 1, wherein $R_3$ is formula (b).
9. The compound of claim 8, wherein $R_6$ and $R_7$ are each alkyl$_{(C\leq 8)}$.
10. The compound of claim 9, wherein $R_6$ and $R_7$ are each methyl.
11. The compound of claim 8, wherein $R_8$ and $R_9$ are each hydrogen.
12. The compound of claim 11, further defined as:

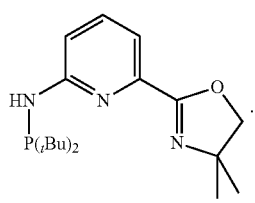

13. The compound of claim 1, wherein $R_3$ is formula (c).
14. The compound of claim 13, further defined as:

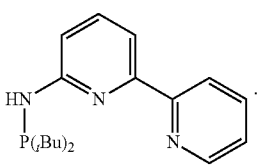

15. The compound of claim 1, wherein $R_3$ is formula (d).
16. The compound of claim 15, further defined as:

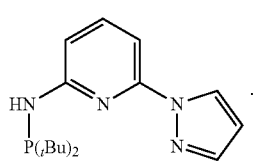

17. The compound of claim 15 wherein $R_{11}$ and $R_{12}$ are each alkyl$_{(C\leq 8)}$.
18. The compound of claim 17, further defined as:

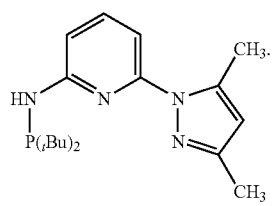

19. The compound of claim 1, further defined as:

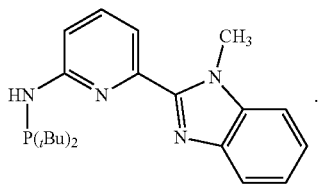

20. A complex comprising a ligand and a metal or metal ion, wherein the ligand is a compound according to claim 1, or a deprotonated version thereof, and the ligand is chemically bound to the metal or metal ion in a 1:1 ratio.

21. The complex of claim 20, wherein the metal or metal ion is a group 8 metal or metal ion.

22. The complex of claim 21, wherein the metal or metal ion is based on ruthenium.

23. The complex according to claim 20, wherein the complex further comprises a second ligand, wherein the second ligand is chloride.

24. The complex according to claim 20, wherein the complex further comprises a third ligand, wherein the third ligand is carbon monoxide.

25. The complex of claim 24, further defined by the formula:

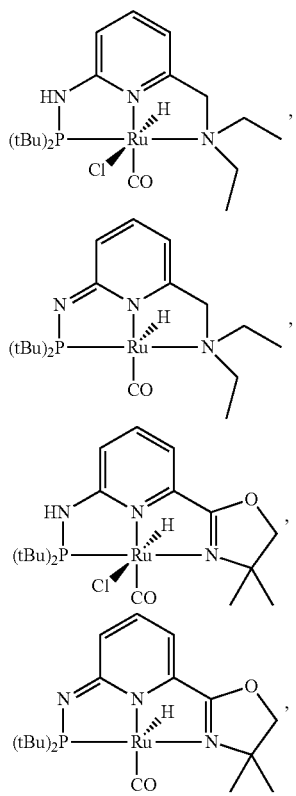

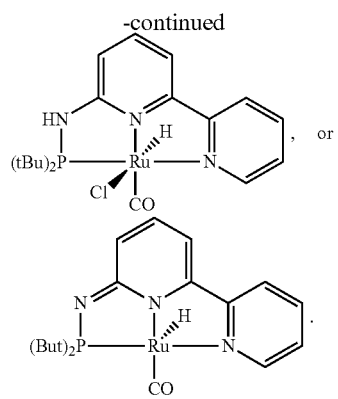

26. The complex of claim 20, wherein the metal or metal ion is a group 9 metal or metal ion.

27. The complex of claim 26, wherein the metal or metal ion is based on cobalt.

28. A method for the preparation of an ester of Formula III comprising reacting two or more alcohols of Formula II:

in the presence of a catalyst to make an ester of Formula III:

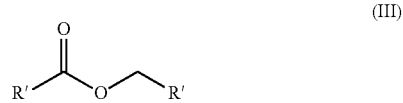

wherein:
R' is alkyl$_{(C\leq 8)}$, substituted alkyl$_{(C\leq 8)}$, aryl$_{(C\leq 8)}$, substituted aryl$_{(C\leq 8)}$, aralkyl$_{(C\leq 8)}$ or substituted aralkyl$_{(C\leq 8)}$; and
the catalyst is a complex according to claim 20.

29. A method for the preparation of an imine of Formula V comprising reacting two or more alcohols of Formula II:

in the presence of a catalyst to make an imine of Formula V:

wherein:
R' is alkyl$_{(C\leq 8)}$, substituted alkyl$_{(C\leq 8)}$, aryl$_{(C\leq 8)}$, substituted aryl$_{(C\leq 8)}$, aralkyl$_{(C\leq 8)}$ or substituted aralkyl$_{(C\leq 8)}$; and
the catalyst is a complex according to claim 20.

* * * * *

UNITED STATES PATENT AND TRADEMARK OFFICE
CERTIFICATE OF CORRECTION

PATENT NO. : 8,598,351 B2  
APPLICATION NO. : 13/528481  
DATED : December 3, 2013  
INVENTOR(S) : Kuo-Wei Huang et al.

Page 1 of 1

It is certified that error appears in the above-identified patent and that said Letters Patent is hereby corrected as shown below:

In the Claims:

Column 32, claim 7 on line 8; claim 12 on line 25; claim 14 on line 38; claim 16 on line 50; and claim 18 on line 63, the compound "P($_t$Bu)$_2$" should read --P(tBu)$_2$--.

Column 33, claim 19 on line 8, the compound "P($_t$Bu)$_2$" should read --P(tBu)$_2$--.

Column 34, claim 25 on line 13, the compound "(But)$_2$P" should read --(tBu)$_2$P--.

Signed and Sealed this  
Twenty-fifth Day of March, 2014

Michelle K. Lee  
*Deputy Director of the United States Patent and Trademark Office*